United States Patent [19]

Ali et al.

[11] Patent Number: 4,684,622
[45] Date of Patent: Aug. 4, 1987

[54] COMPOSITIONS AND METHODS FOR PRODUCING VASODILATION AND ANTIOXYTOCIC ACTIVITY

[75] Inventors: Fadia E. Ali, Cherry Hill, N.J.; William F. Huffman, Malvern, Pa.

[73] Assignee: SmithKline Beckman Corporation, Philadelphia, Pa.

[21] Appl. No.: 853,503

[22] Filed: Apr. 18, 1986

Related U.S. Application Data

[62] Division of Ser. No. 673,828, Nov. 21, 1984, Pat. No. 4,599,324.

[51] Int. Cl.[4] .............................................. A61K 37/02
[52] U.S. Cl. ...................................................... 514/11
[58] Field of Search ......................................... 514/11

[56] References Cited

U.S. PATENT DOCUMENTS 3,941,763   3/1976   Sarantakis ........................... 514/800
4,599,324   7/1986   Ali et al. ............................. 514/11

OTHER PUBLICATIONS

Rudinger, *Peptide Hormones*, Parsons (ed.), U. Park Press, Baltimore, 1976, pp. 1–7.

*Primary Examiner*—Johnnie R. Brown
*Assistant Examiner*—F. T. Moezie
*Attorney, Agent, or Firm*—Mark R. Daniel; Janice E. Williams; Alan D. Lourie

[57] ABSTRACT

Vasopressin derivatives having $V_1$ and oxytocin antagonist activity whose structures are characterized by a Mpa unit at position 1 and a des-Pro unit at position 7 are prepared by standard peptide synthetic methods also using an oxidative cyclization of a dimercaptan. Representative species are [1-deaminopenicillamine-2-(O-methyl)-tyrosine-7-desproline-8-arginine-9-desglycine]vasopressin or [1-β-mercaptopropionic acid-2-D-(O-ethyl)tyrosine-3-isoleucine-4-threonine-7-desproline-8-arginine-9-desglycine]-vasopressin.

7 Claims, No Drawings

COMPOSITIONS AND METHODS FOR PRODUCING VASODILATION AND ANTIOXYTOCIC ACTIVITY

This is a division of application Ser. No. 673,828 filed Nov. 21, 1984, now U.S. Pat. No. 4,599,324.

This invention relates to cyclic peptides which have vasopressin (VSP) antagonist activity. More specifically, these new chemical compounds have VSP or OXT-like structures which are characterized by (1) the lack of a prolyl unit at position 7 and (2) an acyclic β-mercaptopropionic acid residue at position 1. Representative compounds of this new generic group have demonstrated weak $V_2$-antagonistic activity while maintaining $V_1$-antagonistic activity in good degree.

BACKGROUND OF THE INVENTION

A number of synthetic modifications of the vasopressin and oxytocin structures have been reported to give antagonistic activities. Such structures contain units which are derived from β-mercapto-β,β-dialkylpropionic acid, for example, deamino-penicillanic acid or β-mercaptopropionic acid, substituted for the cysteine unit at position 1 of the structure of the natural product: J. Loweridge et al., J. Med. Chem. 22 565 (1979); M. Manning et al., J. Med. Chem. 20 1228 (1977); K. Bankowski et al., J. Med. Chem. 21 350 (1978); H. Schulz et al., J. Med. Chem. 9 647 (1966).

Ferring, A. B., European Patent No. 112,809-A, discloses that certain oxytocin compounds with Mpr at position 1 have anti-OXT activity.

Later studies by M. Manning et al., J. Med. Chem. 25 (1982) and Peptides: Chemistry, Structure and Biology (Ann Arbor Sciences) 737 (1975), demonstrated that no clearly consistent pattern of increasing or decreasing antagonist potency has emerged but, in most of the series studied, the β,β-diethyl and β,β-cyclopentamethylene propionic acid units at position 1 were more active than were the lower homologues, see column 1 on page 411 of the first reference.

We have previously found that removing the proline unit from the tail units, at position 7, on 1-Pmp-VSP structures gave compounds which retained the VSP antagonist activity of the parent compounds, F. Ali et al., Ser. Nos. 586,933 and 586,934, both filed on Mar. 7, 1984 and now allowed. Now, we have found that removing the proline from a 1-dPen or Mpr-VSP derivative gives strong $V_1$-antagonism with a shift in the $V_1:V_2$ ratio to the former.

In the description herein and in the claims, the nomenclature common in the art of peptide and, more specifically, vasopressin chemistry is used. When no configuration is noted, the amino acid unit is in the L, or naturally occuring, form. The thio members of the β-mercaptopropionic acid (1) and cysteine (6) units are added for clarity in certain structural formulas.

Exemplary of the peptide art designations used herein are the following: dPen, β-mercapto-β-β-dimethylpropionic acid; Mpr, β-mercaptopropionic acid; Thr, threonine; Orn, ornithine; OXT, oxytocin; Abu, α-aminobutyric acid; Chg, cyclohexylglycine; Cha, cyclohexylalanine; Pba, α-aminophenylbutyric acid; Gln, glutamine; Gly, glycine; Tyr, tyrosine; Phe, phenylalanine; Val, valine; Ile, isoleucine; Nle, norleucine; Leu, leucine; Ala, alanine; Lys, lysine; Arg, arginine; Harg, homoarginine; Asn, asparagine; Tos, tosylate; BHA, benzhydrylamine; DIEA, diisopropylethylamine; 4-MeBzl, 4-methylbenzyl; TFA, trifluoroacetic acid; DCC, dicyclohexylcarbodiimide; HBT, 1-hydroxybenzotriazole; ACM, acetamidomethyl; Mpa, generic β-mercaptopropionic acids.

DESCRIPTION OF THE INVENTION

The des-Pro-vasopressin-like compounds of the invention are illustrated by the following structural formula:

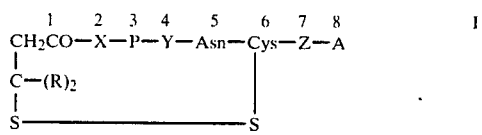

in which:

P is Phe, Ile, Phe(4'-Alk), Tyr or Tyr(Alk);

X is a D or L isomer of Val, Nva, Leu, Ile, Pba Phe, Phe(4'-Alk), Trp, Nle, Cha, Abu, Met, Chg, Tyr or Tyr(Alk);

Y is Val, Ile, Abu, Ala, Chg, Gln, Lys, Cha, Thr, Nle, Phe, Leu or Gly;

Z is a D or L isomer of Arg, Harg, Leu, Lys or Orn;

A is Gly(NH$_2$), Gly, Gly(NH-Alk), OH, NH$_2$ or NHAlk; and

R is, each, hydrogen or methyl; or a pharmaceutically acceptable salt, prodrug ester or complex thereof.

"Alk" in formula 1 and hereafter represents a lower alkyl of 1-4 carbons which may be a substituent which is optionally attached either to the amide nitrogen at A, to a phenyl of an amino acid unit such as Phe at position 2 or 3 or to the oxygen substituent such as that of a tyrosine unit when the latter is present at position 2. Such alkyl substituents include methyl, ethyl, n-propyl, isopropyl or butyl. Preferably, Alk is methyl or ethyl. "Bzl" represents benzyl.

When the term, "vasopressin" or "VSP", is used, it means L-arginine vasopressin (AVP) unless otherwise modified to indicate a D-arginine, leucine, homoarginine, lysine or ornithine-containing vasopressin. Certain antagonists which have structures related to oxytocin (OXT) are also included in this invention.

In the compounds represented by formula I, those with structures having dPen at position 1, a L unit at 2 and an arginine at 7 are preferred for selective VSP $V_1$-antagonism, which is manifested by vasodilation.

The β-mercaptopropionic acid unit at position 1, Mpa$^1$, includes the β,β-dimethyl congener as well as the β-methyl congener in the form of one of its separated isomers or a mixture of isomers.

A subgeneric group of compounds of this invention comprises compounds of formula I in which P is Phe, X is Tyr or Tyr(Alk); Y is Ile or Gln; A is GlyNH$_2$ or NH$_2$; each R is methyl and Z is Arg, Harg, D-Arg, Orn or Leu.

Also included in this invention are various derivatives of the compounds of formula I such as addition salts, prodrugs in ester or amide form and complexes. The addition salts may be either salts with pharmaceutically acceptable cations such as NH$_4^\oplus$, Ca$^{\oplus\oplus}$, K$^\oplus$ or Na$^\oplus$ at a terminal acid group, when present, or with a pharmaceutically acceptable salt at a basic center of the peptide (as in the Arg or Harg units). The acetate salt forms are especially useful although hydrochloride, hydrobromide and salts with other strong acids are useful. In the isolation procedures outlined in the Examples, the peptide product is often isolated as the acetate salt. The compounds also form inner salts or zwitter ions as when a free terminal carboxy group is present.

Prodrugs are derivatives of the compounds of formual I which degrade to the parent compound in vivo. The ester prodrug forms are, for example, lower alkyl esters of the acids of formula I which have from 1-8 carbons in the alkyl radical or aralkyl esters which have 6-12 carbons in the aralkyl radical such as various benzyl esters. Other latentiated derivatives of the compounds of formula I will be obvious to those skilled in the art. "Complexes" include various solvates, such as hydrates or alcoholates, or those with supporting resins, such as a Merrifield resin.

The compounds of formula I are prepared by cyclizing a linear peptide intermediate of this invention by means of the two mercapto groups located, respectively, in the cysteine unit at position 6 and in the $\beta$-mercaptopropionic acid unit at position 1. The cyclization reaction occurs in the presence of a mild oxidizing agent which, at high dilution, is capable of oxidizing intramolecularly the dimercaptan to a disulfide.

Oxidation of the following linear peptide;

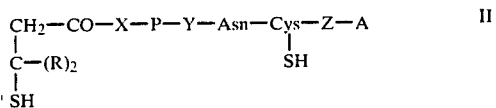

II in which R, P, X, Y, Z, and A are as defined for formula I, but also in which Z is a single bond when A is Gly or OH, is carried out as described generally above. For example, an excess of an alkali metal ferricyanide, such as potassium or sodium ferricyanide, is used. The linear intermediate is dissolved in a suitable unreactive solvent, preferably in an aqueous solvent, at a neutral pH, about 7-7.5. The reaction is run at ambient temperature, or lower, until substantially complete. Lower alcohols, such as methanol, may be added. Preferably, the concentrations of the linear peptide dimercaptan and the oxidizing agent are low, say 0.01 molar concentration of oxidizing agent in several liters of aqueous solution to cyclize 1-6 grams of dimercaptan.

Other mild oxidation agents having an oxidation potential roughly equivalent to ferricyanide may also be used for the ring closure reaction. Oxygen or iodine are alternatives. Of course, one skilled in the art will recognize that certain cyclization methods are not appropriate if an interfering reaction site is present in the structure of the starting material of formula II. The linear mercaptan starting material may or may not have protecting groups common the art present at the various amino acid units or at the mercapto positions. In the former case, the protecting groups are removed after cyclization. In the case of the ACM-SH protecting groups, removal of the protective group and cyclization may both be accomplished using iodine in aqueous methanol. Usually, however, the free linear peptide is cyclized.

The desired cyclic des-proline peptides of formula I are conveniently isolated by acidifying the aqueous oxidation mixture, such as using glacial acetic acid, and passing the reaction mixture over an ion-exchange chromatographic column, for example, over a weakly acid, acrylic resin column with acid elution, or by gel filtration over a bead-formed gel prepared by cross-linking dextran with epichlorohydrin. Often, the acetate salt is isolated by this method.

In an alternative reaction sequence for preparing the compounds of this invention, the intermediate of formula II in which one or both tail units is missing is cyclized as described above. The cyclized product is, then, condensed in one or two optional reactions with the protected amino acid or dipeptide units, which are defined as Z and A for formula I, to extend the tail portion of the structure. Reaction conditions for such tail unit attachment are those of any amide producing method known to the peptide art as described herein. Particularly, reaction of the tail amino acids, whose carboxylic acid group is protected as described, with the 6-Cys acid in the presence of dicyclohexylcarbodiimide and HBT is used. The protecting groups which may be present on the cyclic Cys acid or the tail units are then removed to give the products of this invention. Reaction conditions should be selected to minimize racemization of the Cys unit as known to the art.

The important intermediates of formula II, in free or protected form are conveniently prepared using solid-phase methods of peptide synthesis as discussed in M. Manning et al., J. Med. Chem. 25 46 (1982). A commercial benzhydrylamine support resin (BHR) is used to prepare the amide end products of formula I, i.e. in which A is Gly(NH$_2$), (the amides) and a chloromethyl support resin (CMR) is used to prepare the acid compounds of formula I, i.e. in which A is Gly, (the acids). Solution or enzymatic synthetic methods can also be used.

The peptide chain of the linear peptides of formula II is built up, stepwise, proceeding from unit 7 or 8 working toward the characterizing unit 1. Each unit is properly protected as known in the peptide art and as described below. The sequence of step reactions is conveniently carried out in a Beckman 990-B peptide synthesizer without isolation of each intermediate peptide. The details of the overall synthetic procedure are in the working examples presented hereinafter.

The various amino acids, which are consecutively added to the resin supported chain are protected as known to the art. For example, the Boc protecting group is used for an amino group especially at the α-position of the amino acid; ethylcarbamoyl, adamantyl, t-butyl, acetamidomethyl, trityl or an optionally substituted benzyl, for the mercapto groups at the propionic acid and Cys units; nitro; carbobenzoxy, methylene-2-sulfonyl or tosyl for the Arg unit; and ethyloxycarbonyl or an optionally substituted carbobenzoxy(Z) for the Orn, Tyr, or Lys units. The protective groups should, most conveniently, be those which are easily removed, such as, using acid treatment for the tert.-butyloxycarbonyl (Boc) group, sodium-liquid ammonia or modified catalytic hydrogenation for the benzyl or carbobenzoxy groups.

The protected linear peptide intermediate is split from the carrying resin matrix, for example, by using ammonia in an aqueous miscible solvent, and, then, is treated to remove the protective groups, such as by using sodium-liquid ammonia. This procedure gives the amide derivative of the linear hepta- or octapeptide.

More conveniently, the two steps are combined by treating the resin supported peptide with anhydrous hydrogen fluoride using a suitable carbonium ion scavenger, such as anisole, to give the des-proline dPen$^1$ or Mpr$^1$ peptide intermediate of formula II in good yield.

The compounds of this invention have potent $V_1$-$V_2$ vasopressin antagonist activity with a shift toward the $V_1$-receptors. Vasopressin is primarily known to contribute to the anti-diuretic mechanism of action within the kidney. When the action of these compounds antagonizes that of the natural anti-diuretic hormone (ADH), the body excretes water due to an increased permeability of the terminal portions of the renal tubule. This mechanism of action is at the vasopressin receptors [$V_2$-receptors] located on the plasma membrane of certain renal epithelial cells.

Any patient suffering from the syndrome of inappropriate antidiuretic hormone secretion (SIADH) or from an undesirable edematous condition is a target for compounds which have substantial $V_2$-antagonist activity. Examples of clinical conditions indicated for such compounds include hypertension, hepatic cirrhosis, congestive heart failure or a component of any traumatic condition resulting from serious injury or disease.

The second group of vasopressin receptors, which are more important targets of this invention, are those affecting the smooth muscle tissues of the blood vessels or of the uterus. Vasopressin or oxytocin are natural stimulants of these effectors which result in pressor effects on the cardiovascular system and stimulation of the uterus, respectively. These receptors are called generically $V_1$ receptors for the purposes of this disclosure. The compounds of the present invention antagonize the activity of vasopressin and oxytocin at their receptor sites discussed above.

The compounds of the present invention are, therefore, antagonists at $V_1$ receptor sites. In fact, the $V_1$-$V_2$ ratio of activities of the compounds of this invention is shifted to give potent $V_1$ antagonism with very weak $V_2$ antagonism. Especially active $V_1$ antagonists are the des-Pro-dPen compounds of formula I in which X is a tyrosyl residue and Y is a glutamine residue.

These compounds, therefore, have selective vasodilation activity which is of benefit in dilating arterial systems in which vasopressin is a mediator. The pharmacological activity is manifested in treating hypertension, shock or cardiac insufficiency. They are used in conjunction with ACE inhibitors, α-blockers or β-blockers.

The compounds of formula I which have amino acid units other than at position 1 which resemble those of oxytocin have especially potent anti-oxytocic activity. Therefore, such compounds are particularly useful to relax uterine tissues or dry up milk production. Exemplary of such compounds are the des-Pro-Mpr compounds of formula I in which Z is arginine or ornithine; X is a D-Tyr(alk); P is isoleucine; and Y is glutamine or threonine.

The compounds of this invention, therefore, are mainly used to induce selective vasodilation as noted above or to induce antioxytocic activity in patients in need of such antagonist treatment by administration internally, particularly parenterally or by insufflation, to said patients. A nontoxic but effective quantity of the chosen compound is preferably combined with a pharmaceutical carrier. Dosage units contain a nontoxic, effective quantity of the active ingredient selected from the range 0.05–50 mcg/kg, preferably 1–15 mcg/kg, based on a 70 kg patient. The dosage units are administered from 1 to 5 times daily or by continuous intravenous drip.

The pharmaceutical compositions of this invention, which contain an active ingredient of formula I, comprise a dosage unit quantity as described above dissolved or suspended in a standard liquid carrier. Such a carrier is isotonic saline. The composition is often used in an ampoule or a multiple dose vial suitable for parenteral injection, such as for intravenous, subcutaneous or intramuscular administration. A composition for insufflation may be similar but is often administered in a metered dose applicator or inhaler. Pulverized powder compositions may be used along with oily preparations, gels, buffers for isotonic preparations, emulsions or aerosols.

Antagonistic activity of the $V_1$-vasopressin receptors is determined in a protocol which measures the reversal of the vasopressin-induced contraction of rat thoracic aorta tissue. This is expressed as $K_B$ (nM) in the table below. Such anti-pressor activity is confirmed in a similar in vitro protocol using the plasma membranes of rat liver. $V_2$-vasopressin antagonism is determined as receptor binding ability measured by inhibition of 3H-LVP binding ($K_B$ as nM), by inhibition of adenylate cyclase activation by vasopressin in the medullary tissue of hog kidneys (Ki as nM) or in vivo in the hydropenic rat protocol ($ED_{300}$ μg/kg). These procedures are described in the literature: F. Stassen et al., J. Pharmacology and Experimental Therapeutics, 223 50 (1982); F. Stassen et al., 1st International Conference on Diuretics, Miami, Fla., March (1984). Antagonistic activity at oxytocin receptors is determined in the isolated rat uterus protocol: W. Sawyer, et al., Endocrinology 106 81 (1979); P. Melin, et al., J. of Endocrinology 88 173 (1981).

TABLE 1

| Compound | Representative Antagonist Activity | | | | |
|---|---|---|---|---|---|
| | Pig $V_2^a$ Ki (nM) | Pig $V_2^a$ $K_B$ (nM) | Rat $V_1^b$ $K_B$ (nM) | Rat $V_1^c$ $K_B$ (nM) | Rat $OXT^d$ $K_B$ (nM) | Rat $V_2^e$ $ED_{300}$ (μg/kg) |
| A | — | 3000 | 38 | 5.69 | 32.6 | >5959 |
| B | — | 3300 | 37 | 1.48 | 18.9 | >5977 |
| C | — | 350 | — | $0.0072^f$ | 1.88 | — |
| D | — | 1600 | — | — | 11.4 | ~2037 |
| E | — | 4100 | — | — | 17.7 | >5018 |
| F | agonist | 70 | 2.9 | — | — | — |
| G | 210 | 369 | 0.48 | 0.026 | — | >5000 |

[a]Medullary pig kidney tissue,
[b]Rat liver membrane,
[c]Rat aortic ring tissue,
[d]Rat uterus,
[e]Hydropenic rat,
[f]estimated; compound non-competitive.

dPen—Tyr(Me)—Phe—Gln—Asn—Cys—Arg($NH_2$)  A.
|_____|

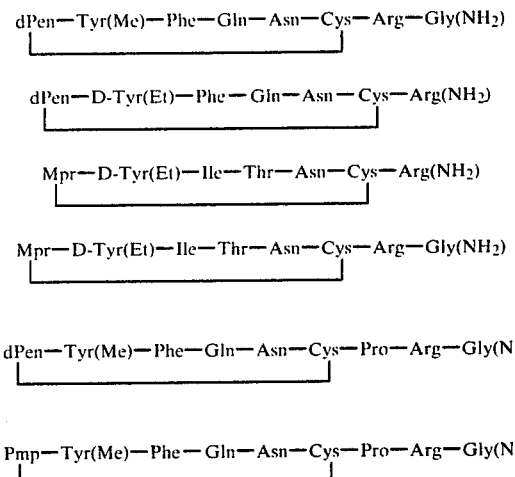

B. dPen—Tyr(Me)—Phe—Gln—Asn—Cys—Arg—Gly(NH₂)

C. dPen—D-Tyr(Et)—Phe—Gln—Asn—Cys—Arg(NH₂)

D. Mpr—D-Tyr(Et)—Ile—Thr—Asn—Cys—Arg(NH₂)

E. Mpr—D-Tyr(Et)—Ile—Thr—Asn—Cys—Arg—Gly(NH₂)

F. dPen—Tyr(Me)—Phe—Gln—Asn—Cys—Pro—Arg—Gly(NH₂)

G. Pmp—Tyr(Me)—Phe—Gln—Asn—Cys—Pro—Arg—Gly(NH₂)

The data in Table 1 demonstrate a shift to potent $V_1$ and OXT antagonistic activity from the potent $V_2$-receptor antagonism represented by a representative Pmp[1] compound. Some $V_2$-antagonism is however still demonstrated by the compounds of this invention.

The following examples are intended solely to teach the preparation of the compounds of this invention. All temperatures are in degrees Centigrade.

EXAMPLE 1

Solid Phase Synthesis of Supported Linear Peptide-BHA Resin Starting Material For the solid phase synthesis of the titled resin-supported peptides, a 7 or 8-position unit-resin material, for example, Boc. Arg(Tos)BHA resin (1.00 mmol/g of resin), was used as a starting material. It was prepared by reacting Boc-Amino Acid-(Tos if necessary), 3 mmol, with the benzhydrylamine resin, 1.0 mmol, in dimethylformamide for two hours. The benzhydrylamine resin as a free base was swelled in methylene chloride overnight. It was washed once with 7% diisopropylethylamine (DIEA) in methylene chloride, then 6×1 min. with methylene chloride, and finally 2×1 min. with predried dimethylformamide. The loading of BOC-amino acid on the resin was carried out twice on the shaker using 1-hydroxybenzotriazole (HBT, 6 mmol), and dicyclohexylcarbodiimide (DCC, 3 mmol). A quantitative ninhydrin test and amino acid analysis were performed routinely after loading to determine the percentage loading on the resin.

The appropriately protected amino acids were coupled sequentially on the Boc-amino acid-resin using the Beckman peptide synthesizer 990-B or a shaker. The program used for each coupling, except Boc-Asn and Mpa(4-MeBzl), was as follows:

(1) Washed with methylene chloride (3 times, 1 min).
(2) Prewashed with 50% trifluoroacetic acid in methylene chloride (1 time, 1 min).
(3) Deprotection with 50% trifluoroacetic acid in methylene chloride (20 min).
(4) Washed with methylene chloride (3 times, 1 min).
(5) Prewashed with 7% DIEA in methylene chloride (1 time, 1 min).
(6) Neutralized with 7% DIEA in methylene chloride (1 time, 10 min).
(7) Washed with methylene chloride (3 times, 1 min).
(8) Protected amino acid (3 mmol) in methylene chloride, followed by addition of DCC, 3 mmol, 10 ml of 0.3M in methylene chloride, and coupling for two hours.
(9) Washing with methylene chloride (3 times, 1 min).
(10) Washing with ethanol/methylene chloride (1:1) (3 times, 1 min).
(11) Washing with methylene chloride (3 times, 1 min).

In case of coupling of Asn moiety, 1-hydroxybenzotriazole (HBT, 6 mmol) was used, 10 ml of 0.6M in dimethylformamide. Dry dimethylformamide was also used as solvent when Mpa (4-MeBzl) was coupled into the peptide resin, using 4-dimethylaminopyridine (DAP, 3 mmol). Completion of each coupling reaction was monitored by the ninhydrin test. The p-methylbenzyl group was used to protect the thiol groups of Cys and the β-mercaptopropionic acid (Mpa) moieties.

The benzhydrylamine resin was analyzed by nitrogen analysis to fall within 0.72–1.03 mmol per 1 gram. Each protected amino acid unit was purchased from commercial sources or synthesized by known procedures. Successful coupling incorporated 0.4 to 0.732 mmole per gram of the first amino acid.

EXAMPLE 2

dPen—Tyr(Me)—Phe—Gln—Asn—Cys—Arg—Gly(NH₂)

The protected peptide intermediate resin, dPen-(4-MeBz)-Tyr(Me)-Phe-Gln-Asn-Cys(4-MeBz)-Arg(Tos)-BHA resin (1.85 g, obtained from 1.0 mmol/g amine/resin ($N_2$-analysis) using a Beckman peptide synthesizer, 990-B), was reacted with anhydrous hydrogen fluoride (30 ml) in the presence of 3.0 ml of anisole at 0° for 50 min. After evaporation in vacuo to dryness, the residue was treated with anhydrous diethyl ether. The crude peptide was extracted with dimethylformamide (90 ml) and 33% acetic acid (90 ml) into 3.5 l of de-aerated water previously adjusted to pH 4.5. The aqueous diluted disulfhydryl octapeptide was cyclized using 0.01M potassium ferricyanide solution at pH 7.12 until color persisted for 30 minutes. After the completion of the oxidation reaction, the pH of the solution was adjusted to 4.5 using glacial acetic acid. This solution was passed through a weakly acid acrylic resin (Bio-Rex 70) column (2.5×12 cm) slowly. The column was eluted with pyridine-acetate buffer (30:4:66, pyridine/glacial acetic acid/water). The pyridine acetate solution was then removed by distillation in vacuo. The residue was lyophilized from 5% acetic acid to give 610 mg (60%) of crude titled peptide.

Purification:
(1) Counter-current distribution (CCD): Sample 610 mg, n-BuOH/HOAc/H₂O, (4:1:5), 240 transfers. Tubes 106-148 gave 293 mg of product.
(2) Gel Filtration, Sephadex-G-15, 0.2M HOAc: 100 mg gave fraction a, 46 mg, and fraction b, 23 mg of pure material.

Physical Data:
$C_{44}H_{63}N_{13}O_{11}S_2$; molecular weight, 1013.393
Fast atom bombardment,
mass spectra (FAB): $(M=H)^{\oplus}$ 1014, $(M-H)^{\ominus}$ 1012
Amino acid
Analysis (AAA): Asp (1.00), Glu (1.19), Gly (1.10), Cys (0.45), Tyr (0.60), Phe (1.09), Arg (0.97)

Peptide Content: 63.4% (amino acid content), 84.93% ($N_2$-analysis).
Chromatography:
1. Thin layer chromatography (TLC)
   (a) B/A/W/E (1:1:1:1), $R_f$=0.66
   (b) B/A/W/P (15:3:3:10), $R_f$=0.34
2. High pressure liquid chromatography (HPLC) "Altex" ultrasphere ODS column, 5μ, 4.5 mm×25 cm 0.1% TFA a, $CH_3CN$ b:
   (a) Gradient, 80 a/20 b to 50:50, a/b, in 15 min.
      k'=4.72
   (b) Isocratic, 70 a:30 b
      k'=2.6.

EXAMPLE 3

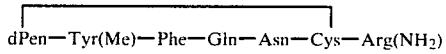
dPen—Tyr(Me)—Phe—Gln—Asn—Cys—Arg(NH₂)

The protected peptide-resin, dPen(4-MeBzl)-Tyr(-Me)-Phe-Gln-Asn-Cys(4-MeBzl)-Arg(Tos)-BHA-resin (2.0 g, obtained from 1.0 mmol/g of amine/resin ($N_2$-analysis), 0.732 mmol/g incorporation of Boc-Arg(Tos) (AAA), using the manual shaker), was reacted with 30 ml of anhydrous hydrogen fluoride in the presence of 3.0 ml of anisole at 0° for 50 minutes. After evaporation in vacuo to dryness, the residue was treated with anhydrous diethyl ether. The crude peptide was extracted with dimethylformamide (75 ml), and 33% acetic acid (75 ml) and taken into 3.5 liter of de-aerated water which had been previously adjusted to pH 4.5. The aqueous diluted disulfhydryl heptapeptide was oxidatively cyclized using 0.01M potassium ferricyanide solution at pH 7.12 until color persisted for 30 minutes. After the completion of the oxidation reaction, the pH of the solution was adjusted to 4.5 using glacial acetic acid. This solution was passed through a weakly acid acrylic resin (Bio-Rex-70) column (2.5×10 cm) slowly. The column was eluted with pyridine-acetate buffer (30:4:66), pyr/HOAc/$H_2O$). The pyridine acetate solution was removed in vacuo. The residue was lyophilized from B 10% acetic acid to give 525 mg (75%) of crude titled peptide.
Purification:
(1) Counter-current distribution (CCD):
   Sample 525 mg, n-BuOH/HOAc/$H_2O$ (4:1:5), 240 transfers
   (a) Tubes 128-152, 121.3 mg
   (b) Tubes 118-127+153-170, 118 mg pure
(2) Gel Filtration, "Sephadex" G-15, 0.2M HOAc: 89.66 mg from 1a, obtained (1) Fr, 42 mg, (b) Fr, 30.5 mg pure
Physical Data:
$C_{42}H_{60}N_{12}O_{10}S_2$; molecular weight, 956.371
FAB: (M+H)⊕957, (M−H)⊖955,
AAA: Asp (1.00), Glu (1.07), Cys (0.48), Tyr (0.57), Phe (0.99), Arg (0.89)
Peptide Content: 72.2% (AAA), 82.54% ($N_2$-analysis).
Chromatography:
1. TLC; B/A/W/E (1:1:1:1), $R_f$=0.76
2. HPLC; "Altex" ultrasphere ODS column, 5μ, 4.5 mm×25 cm (a) 0.1% TFA (b) $CH_3CN$
   (a) Gradient; 80 a/20 b to 50 a/50 b in 15 min, k'=5.67
   (b) Isocratic; 70 a:30 b, k'=2.93

EXAMPLE 4

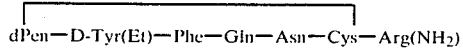
dPen—D-Tyr(Et)—Phe—Gln—Asn—Cys—Arg(NH₂)

The protected peptide resin, d-Pen(4-MeBzl)-D-Tyr-(Et)-Phe-Gln-Asn-Cys(4-MeBzl)-Arg(Tos)-BHA-resin (2.56 g which was obtained from 0.72 mmol/g, amine/resin ($N_2$-analysis), 0.4 mmol/g incorporation of Boc-Arg(Tos) (AAA) using an automated peptide synthesizer, Beckman 990-B), was reacted with 30 ml of anhydrous hydrogen fluoride in the presence of 3-4 ml of anisole at 0° for one hour. After evaporation of excess hydrogen fluoride in vacuo to dryness, the residue was treated with anhydrous diethyl ether. The crude peptide was extracted with dimethyl formamide (75 ml) and 40% acetic acid (75 ml) and taken into 3.5 l of deaerated water which had been previously adjusted to pH 4.5. The aqueous diluted disulfhydryl heptapeptide was oxidatively cyclized using 0.01M $K_3Fe(CN)_6$ solution at pH 7.17 until color persisted for 30 minutes. After the completion of the oxidation reaction, the pH of the solution was adjusted to 4.5 using glacial acetic acid. This solution was passed through a weakly acid acrylic resin (Bio-Rex 70) column (2.5×10 cm) slowly. The column was eluted with pyridine-acetate buffer (30:4:6, pyr/HOAc/$H_2O$). The pyridine-acetate solution was removed in vacuo, and the residue was lyophilized from 10% acetic acid to give 450 mg (83.85%) of the crude titled peptide.
Purification:
1. Counter-current distribution (CCD): Sample 450 mg, n-BuOH/HOAc/$H_2O$, (4:1:5), 240 transfers
   a. Tubes 154-182, 110.70 mg
   b. Tubes 138-153, 193.44 mg
   C. Tubes 132-137+183-190, 46.98 mg
2. Polyacrylamide resin ("Biogel" P2) column, 10.2M HOAc used 93 mg from 1a obtained (a) Fr 50.71 mg, (b) Fr 27.42 mg pure.
Physical data:
$C_{43}H_{62}N_{12}O_{10}S_2$; molecular weight, 970.372
FAB: (M+H)⊕971, (M-H)⊖969
AAA: Asp (1.00), Gln (0.94), Cys (0.31), Tyr (0.62), Phe (1.00), Arg (0.97)
Chromatography:
1. TLC;
   (a) B/A/W/E (1:1:1:1), $R_f$=0.657
   (b) B/A/W (4:1:5 upper), $R_f$=0.37
2. HPLC; "Altex" Ultrasphere ODS column, 5μ, 4.5 mm×25 cm
   (a) Gradient; 80 a/20 b to 50 a/50 b in 20 min k'=9.01
   (b) Isocratic; 70 a/30 b k'=2.46

EXAMPLE 5

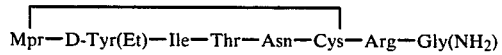
Mpr—D-Tyr(Et)—Ile—Thr—Asn—Cys—Arg—Gly(NH₂)

The protected peptide-resin, Mpr(4-MeBzl)-D-Tyr-(Et)-Ile-Thr(OBzl)-Asn-Cys(4-MeBzl)-Arg(Tox)-Gly-BHA-R (2.33 g, obtained from 0.72 mmol/g amine/resin ($N_2$-analysis), 0.46 mmol incorporation of Boc-Gly (AAA), using an automated peptide synthesizer, Beckman 990-B), was cleaved, deprotected by hydrogen fluoride and oxidatively cyclized, as described above, to give crude titled peptide, 500 mg (87.81%).

Purification:
(1) CCD: Sample 500 mg using BuOH/HOAc/H$_2$O (4:1:5), 240 transfers
   (a) Tubes 138–166, 112.95 mg pure
   (b) Tubes 126–137+167–180, 161.59 mg
   (c) Tubes 122–125+181–190, 87.20 mg
(2) HPLC:

Sample, 53.9 mg (from 1a), "Altex" ODS, 10 mm×25 cm, 5u, flow rate 5 ml/min, 0.1% TFA/CH$_3$CN (60/40), isocratic 220 nm (2.0 AUFS), injection 7.19 mg/400 ml to give 45 mg of pure sample of the titled peptide.

Physical data:

$C_{39}H_{62}N_{12}O_{11}S_2$; Molecular weight, 938.375

FAB: (M+H)$^{\oplus}$939, (M-H)$^{\ominus}$937

AAA: Asp (1.00), Thr (0.75), Gly (0.93), Cys (1.00), Ile (0.79), Tyr (0.55), Arg (0.88).

Peptide Content: 68.7% (AAA); 77.78% (N$_2$-analysis)

Chromatography:
(1) TLC;
   (a) B/A/W/E (1:1:1:1), R$_f$=0.69
   (b) B/A/W (4:1:5 upper), R$_f$=0.446
(2) HPLC; a 0.1% TFA b CH$_3$CN
   (a) Gradient 80 a/20 b to 50 a/50 b in 15 minutes
       k+=3.6
   (b) Isocratic 65 a/35 b
       k'=1.56

EXAMPLE 6

Mpr—D-Tyr(Et)—Ile—Thr—Asn—Cys—Arg(NH$_2$)

The protected peptide resin, Mpr(4-MeBzl)-D-Tyr(Et)-Ile-Thr(OBzl)-Asn-Cys(4-MeBzl)-Arg(Tos)-BHA-R (2.2 g, obtained from 1.0 mmol/g amine/resin (N$_2$-analysis), 0.485 mmol/g incorporation of Boc-Arg(Tos), (AAA), using the manual shaker), was reacted with hydrogen fluoride and oxidized as described previously to give crude titled peptide, 245 mg (57.2%).

Purification:
(1) CCD; n-BuOH/HOAc/H$_2$O (4:1:5), 240 transfers
   (a) Tubes 162–190, 156.75 mg
   (b) Tubes 156–161+191–200, 56.43 mg Physical data:

$C_{37}H_{59}N_{11}O_{10}S_2$; molecular weight, 881.353

FAB: (M+H)$^{\oplus}$882, (M−H)$^{\ominus}$880

AAA: Asp (1.00), Thr (0.85), Cys (0.89), Ile (0.75), Tyr (0.52), Arg (1.27)

Peptide Content: 72.2% (AAA) and 85.58% (N$_2$ analysis).

Chromatography:
(1) TLC;
   (a) B/A/W/E (1:1:1:1), R$_f$=0.63
   (b) B/A/W/P (15:3:3:10), R$_f$=0.66
(2) HPLC; a 0.1% TFA b CH$_3$CN
   (a) Gradient 80 a/20 b to 50 a/50 b in 20 min
       k'=5.34
   (b) Isocratic 65 a: 35 b
       K'=2.0

EXAMPLE 7

Procedure for the general synthesis of the acid end products (I, A is OH) or cyclic acid intermediates (I, A is OH and Z may be a single bond):

Boc-AA-Merrifield resin is made by coupling a Boc-Aa to Merrifield resin using the known cesium salt method to give Boc-AA-OCH$_2$C$_6$H$_4$-resin which is used as the starting material for the synthesis. The synthesis is carried out on the Beckman 990-B peptide synthesizer using the following protocol. Three equivalents of each of the amino acids are dissolved in their appropriate solvents [for example, the Boc derivatives of 4-MeBzl-Cys, Val, Phe and S-4-MeBzl-Mpa in methylene chloride, Asn in dimethylformamide, D-Tyr(Et) or BrZ-D-Tyr in 1:1 methylene chloride/dimethylformamide] and are coupled using an equimolar amount of dicyclohexylcarbodiimide (DCC) and 1-hydroxybenzotriazole (HBT) except for the coupling of 4-MeBzl-Mpa where 1.0 equivalent of dimethylaminopyridine is used as catalyst. The extent of coupling is dermined by qualitative ninhydrin analyses of each aliquot sample and couplings are repeated when necessary. The Boc groups are removed using 1:1 trifluoroacetic acid/methylene chloride and, after washing, the free amine is generated using 5% diisopropylethylamine/methylene chloride. The sequence of the peptide is checked using solid phase sequencing before coupling of the 4-MeBzl-Mpa and its homogeneity confirmed. After the final coupling, the peptide is dried to give the peptide-resin.

1.1 Grams (0.5 mmole) of the peptide resin with 3 ml of anisole is stirred 60 min at 0° (ice bath) in 25 ml of anhydrous liquid hydrogen fluoride (HF). The HF is, then, removed under reduced pressure at 0°. The residue is washed with ethyl ether and the peptide eluted with dimethylformamide, 20% acetic acid and 0.3N ammonium hydroxide.

The filtrate is added to 2 l of degassed water and the pH adjusted to 7.1 with conc. ammonium hydroxide. A 0.01M solution of potassium ferricyanide is then added dropwise with stirring until a faint yellow color persisted (about 41 ml).

The resulted solution is then passed through a flash column (5 cm×15 cm) of a packing of silica gel coated with a C-18 silane. The column is, then, washed with 350 ml of water and the peptide eluted with 500 ml of 1:1 acetonitrile/water (0.25% trifluoroacetic acid) in 20 ml fractions.

Product containing fractions (TLC) are combined and concentrated. The residue is dissolved in conc. acetic acid, diluted with water and lyophilized to yield the acid peptide. The Cys(OH) or Z(OH) intermediates are used, without further purification, for the synthesis of the end product peptides.

[1-dPen-2-Tyr(Me)-4-Gln-7-desPro-8-des-Arg-9-desGly(NH$_2$)]vasopressin (0.3 mmol, prepared as described above) and Arg(NH$_2$) (0.9 mmol) are reacted in dimethylformamide in the presence of dicyclohexylcarbodiimide (0.9 mmol) and 1-hydroxybenzotriazole (1.8 mmol) at 0°–20° for 6 hours. The volatiles are removed under vacuum. The residue is purified as in Example 2 to give [1-dPen-2-Tyr(Me)-4-Gln-7-desPro-7-Arg(NH$_2$)-8-desArg-9-desGly(NH$_2$)]vasopressin.

Reaction of the above Cys(OH) peptide with Arg-Gly(NH$_2$) under similar reaction conditions gives the corresponding dipeptide-tailed vasopressin derivative.

EXAMPLE 8

Substituting Boc-Lys(ClZ) in Example 2 for the arginine unit gives

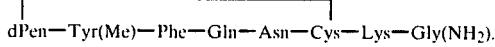
dPen—Tyr(Me)—Phe—Gln—Asn—Cys—Lys—Gly(NH₂).

Substituting Boc-Orn(ClZ) in Example 2 for the arginine unit gives

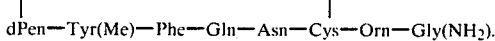
dPen—Tyr(Me)—Phe—Gln—Asn—Cys—Orn—Gly(NH₂).

Substituting Boc-Abu in Example 3 for the Gln unit gives

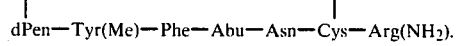
dPen—Tyr(Me)—Phe—Abu—Asn—Cys—Arg(NH₂).

Substituting Boc-Leu for the D-Tyr(Et) unit and D-Arg for the arginine unit in Example 5 gives

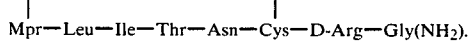
Mpr—Leu—Ile—Thr—Asn—Cys—D-Arg—Gly(NH₂).

Substituting Boc-Chg for the threonine unit in Example 6 gives

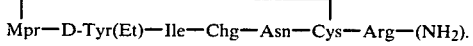
Mpr—D-Tyr(Et)—Ile—Chg—Asn—Cys—Arg—(NH₂).

Substituting Boc-Tyr(BrZ) in Example 6 for the D-Try(Et) unit in Example 6 gives

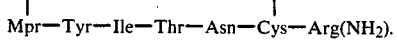
Mpr—Tyr—Ile—Thr—Asn—Cys—Arg(NH₂).

Substituting Boc-α-aminophenylbutyric acid for the Tyr(Me) unit of Example 3 gives

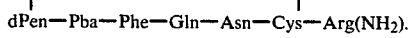
dPen—Pba—Phe—Gln—Asn—Cys—Arg(NH₂).

Other representative compounds which are prepared by the methods of synthesis described above are:

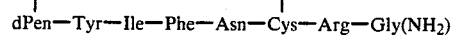
dPen—Tyr—Ile—Phe—Asn—Cys—Arg—Gly(NH₂)

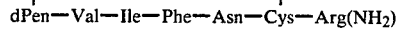
dPen—Val—Ile—Phe—Asn—Cys—Arg(NH₂)

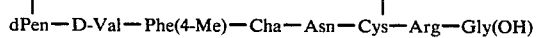
dPen—D-Val—Phe(4-Me)—Cha—Asn—Cys—Arg—Gly(OH)

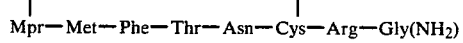
Mpr—Met—Phe—Thr—Asn—Cys—Arg—Gly(NH₂)

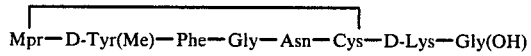
Mpr—D-Tyr(Me)—Phe—Gly—Asn—Cys—D-Lys—Gly(OH)

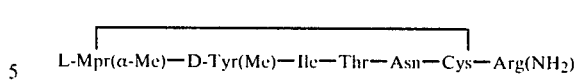
L-Mpr(α-Me)—D-Tyr(Me)—Ile—Thr—Asn—Cys—Arg(NH₂)

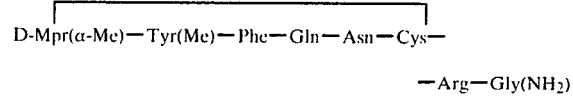
D-Mpr(α-Me)—Tyr(Me)—Phe—Gln—Asn—Cys—
—Arg—Gly(NH₂)

EXAMPLE 9

Parenteral Dosage Unit Compositions

A preparation which contains 10 mcg of the cyclic peptide of Example 2 as a sterile dry powder for parenteral injection is prepared as follows: 10 mcg of the peptide amide is dissolved in 1 ml of an aqueous solution of 20 mg of mannitol. The solution is filtered under sterile conditions into a 2 ml ampoule and lyophylized. The powder is reconstituted before either intramuscular or intravenous injection to a subject suffering from hypertesion or shock susceptible to anti-ADH mechanism of action. The injection is repeated as necessary, from 1-5 times daily or in continuous i.v. drug injection. Other desPropeptides of this invention are made up and used in like manner.

Nasal Dosage Unit Compositions

20 Milligrams of finely ground desPropeptide of this invention such as the product of Example 2 is suspended in a mixture of 75 mg of benzyl alcohol and 1.395 g of a suspending agent such as a commercial mixture of semisynthetic glycerides of higher fatty acids. The suspension is placed in an aerosol 10 ml container which is closed with a metering valve and charged with aerosol propellants. The contents comprise 100 unit doses which are administered intranasally to an edematous subject from 1-6 times a day.

What is claimed is:

1. A pharmaceutical composition having V₁-vasopressin and oxytocic antagonist activity comprising a pharmaceutical carrier and, dispersed therein, an effective therefor but nontoxic quantity of a compound having the formula:

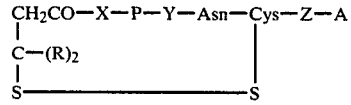

in which:

P is Phe, Ile, Phe(4'-Alk), Tyr or Tyr(Alk);

X is a D or L isomer of Val, Nva, Leu, Ile, Pba, Phe, Phe(4'-Alk), Trp, Nle, Cha, Abu, Met, Chg, Tyr or Tyr(Alk);

Y is Val, Ile, Abu, Ala, Chg, Gln, Lys, Cha, Thr, Nle, Phe, Leu or Gly;

Z is a D or L isomer of Arg, Harg, Leu, Lys or Orn;

A is Gly(NH₂), Gly, Gly(NH-Alk), OH, NH₂ or NHAlk; and

R is, each, hydrogen or methyl, and each of the Alk groups is a lower alkyl of 1–4 carbons, or a pharmaceutically acceptable salt thereof.

2. A composition of claim 1 in which said composition is adapted for parenteral administration and the quantity of the compound is selected from the range of from 0.5–50 mcg/kg.

3. A composition of claim 1 in which the compound is [1-deaminopenicillamine-2-(O-methyl)tyrosine-7-desproline-8-arginine-9-desglycine]vasopressin.

4. A composition of claim 1 in which the compound is [1-β-mercaptopropionic acid-2-D-(O-ethyl)tyrosine-3-isoleucine-4-threonine-7-desproline-8-arginine-9-desglycine]vasopressin.

5. The method of producing vasodilation and antioxytocic activity in a patient in need thereof which comprises administering parenterally or intranasally to said patient a nontoxic, effective therefor quantity of a compound having the formula:

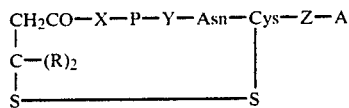

in which:
- P is Phe, Ile, Phe(4'-Alk), Tyr or Tyr(Alk);
- X is a D or L isomer of Val, Nva, Leu, Ile, Pba, Phe, Phe(4'-Alk), Trp, Nle, Cha, Abu, Met, Chg, Tyr or Tyr(Alk);
- Y is Val, Ile, Abu, Ala, Chg, Gln, Lys, Cha, Thr, Nle, Phe, Leu or Gly;
- Z is a D or L isomer of Arg, Harg, Leu, Lys or Orn;
- A is $Gly(NH_2)$, Gly, Gly(NH-Alk), OH, $NH_2$ or NHAlk; and
- R is, each, hydrogen or methyl, and each of the Alk groups is a lower alkyl of 1–4 carbons, or a pharmaceutically acceptable salt thereof.

6. The method of claim 5 in which the compound is [1-deaminopenicillamine-2-(O-methyl)tyrosine-7-desproline-8-arginine-9-desglycine]vasopressin.

7. The method of claim 5 in which the compound is [1-β-mercaptopropionic acid-2-D-(O-ethyl)tyrosine-3-isoleucine-4-threonine-7-desproline-8-arginine-9-desglycine]vasopressin.

* * * * *